United States Patent [19]
Spool et al.

[11] Patent Number: 6,110,151
[45] Date of Patent: Aug. 29, 2000

[54] INFLATION DEVICE

[75] Inventors: Ira Spool, Brooklyn; Karl Dallas Kirk, III; Paul J. Mulhauser, both of New York City; Colin Hart; Glenn H. Wadleigh, both of Queensbury, all of N.Y.

[73] Assignee: Namic USA Corporation, Glen Falls, N.Y.

[21] Appl. No.: 09/133,408

[22] Filed: Aug. 13, 1998

[51] Int. Cl.[7] .................................................. A61M 5/315
[52] U.S. Cl. .............................. 604/218; 604/97; 604/99; 604/181
[58] Field of Search .............................. 604/97–100, 211, 604/121, 228, 181, 187, 224, 218, 220

[56] References Cited

U.S. PATENT DOCUMENTS

| | | | |
|---|---|---|---|
| 4,583,978 | 4/1986 | Porat et al. | 604/208 |
| 4,929,238 | 5/1990 | Baum | 604/208 |
| 5,137,514 | 8/1992 | Ryan | 604/99 |
| 5,147,300 | 9/1992 | Robinson et al. | 604/97 |
| 5,290,260 | 3/1994 | Stines | 604/224 |
| 5,342,304 | 8/1994 | Tacklind et al. | 604/99 |
| 5,466,221 | 11/1995 | Zadini et al. | 604/96 |
| 5,685,848 | 11/1997 | Robinson et al. | 604/97 |
| 5,713,242 | 2/1998 | Kanner et al. | 74/424.8 A |
| 5,800,405 | 9/1998 | McPhee | 604/218 |
| 5,860,955 | 1/1999 | Wright et al. | 604/99 |
| 5,938,642 | 8/1999 | Burroughs et al. | 604/208 |

FOREIGN PATENT DOCUMENTS

| | | |
|---|---|---|
| 0 217 559 | 4/1987 | European Pat. Off. . |
| WO92/06735 | 4/1992 | European Pat. Off. . |
| 0 565 045 | 10/1993 | European Pat. Off. . |
| 297 12 332 | 11/1997 | Germany . |

*Primary Examiner*—Corrine McDermott
*Assistant Examiner*—Cris L. Rodriguez
*Attorney, Agent, or Firm*—Kenyon & Kenyon

[57] ABSTRACT

An inflation device according to the present invention includes a barrel, a piston at least partially disposed within the barrel, and a collar surrounding at least a portion of the barrel. The piston includes a threaded portion. The collar and the barrel are axially movable with respect to one another, with the barrel being biased towards an equilibrium position within the collar by a collar spring. A nut is disposed at least partially within the barrel, the nut including an interior threaded surface and an exterior camming surface. The nut is movable along an axis substantially transverse to the barrel axis, and is biased towards a collar camming surface by a nut spring. When the barrel is in the equilibrium position, the nut is in a locking position in which the interior threaded surface engages the threaded portion of the piston. This prevents free movement of the piston within the barrel. When the barrel is moved from the equilibrium position the collar camming surface deflects the nut so that the piston is freely movable within the barrel.

27 Claims, 13 Drawing Sheets

INFLATION DEVICE

FIELD OF THE INVENTION

The present invention relates to inflation devices, and in particular to inflation devices for use with inflatable members such as balloon catheters.

BACKGROUND INFORMATION

Balloon catheters are used for several medical procedures, including balloon angioplasty and stent delivery. The balloon may be inflated by an inflation device in the general form of a syringe assembly, and in general it is advantageous for the device to be capable of providing rapid inflation or deflation of the balloon while also providing fine adjustment of the balloon pressure. In addition, it is advantageous for the inflation device to maintain the balloon at a desired pressure without force being applied continuously by the operator.

Several inflation devices of the syringe design have been proposed which enable the piston of the syringe to move with respect to the barrel in both a freely reciprocating mode and a threaded or locked mode, for example U.S. Pat. No. 5,137,514 to Ryan and U.S. Pat. No. 5,147,300 to Robinson et al. A device such as described in these patents includes a thread engagement mechanism that may lock the piston into a threaded mode. However, in each case the operator is required to either depress a trigger or move a control button before the thread engagement mechanism is released.

SUMMARY OF THE INVENTION

An inflation device according to the present invention includes a barrel, a piston at least partially disposed within the barrel, and a collar surrounding at least a portion of the barrel. The piston includes a threaded portion. The collar and the barrel are axially movable with respect to one another, with the barrel being biased towards an equilibrium position within the collar by a collar spring. A nut may be disposed at least partially within a recess of the barrel, the nut including an interior threaded surface and an exterior camming surface. The nut may be movable along an axis substantially transverse to the barrel axis, and is preferably biased towards a collar camming surface by a nut spring. When the barrel is in the equilibrium position, the interior threaded surface of the nut is in a locking position which prevents free movement of the piston within the barrel. When the barrel is moved from the equilibrium position the collar camming surface deflects the nut so that the piston is freely movable within the barrel.

DETAILED DESCRIPTION

Figure 1:
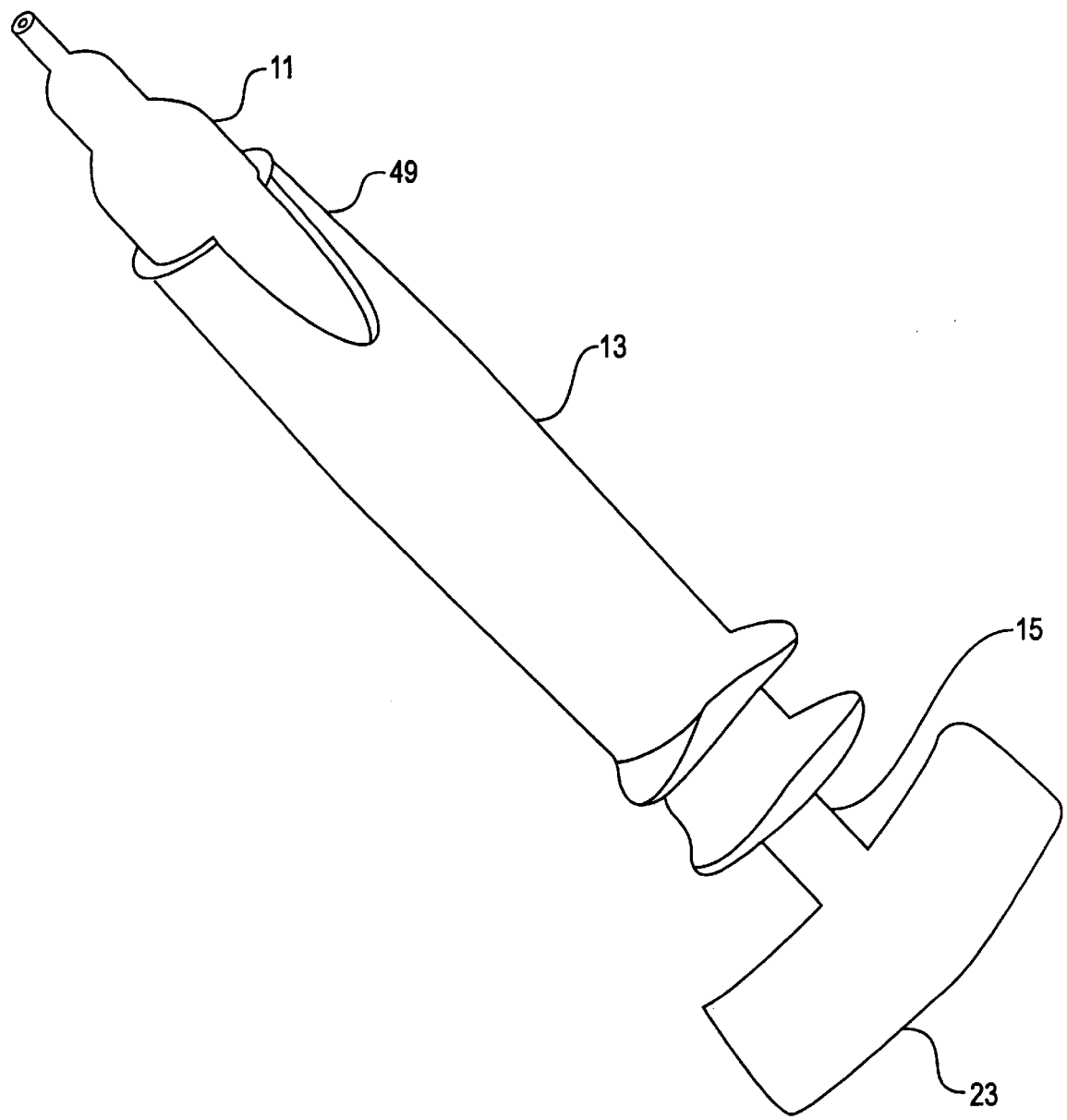
FIG. 1 is a perspective view of an exemplary embodiment of an inflation device according to the present invention.

FIG. 1 illustrates an exemplary embodiment of an inflation device according to the present invention. The exemplary inflation device includes a barrel 11 surrounded by a collar 13. A piston 15 acts in conjunction with barrel 11 to form a syringe assembly, with a handle 23 being attached to a proximal end of piston 15, "proximal" generally designating the portion of the inflation device closer to operator (towards the right in FIGS. 2–4). Via mechanisms described below, barrel 11 is axially movable within collar 13, but biased towards a central equilibrium position. When barrel 11 is in its equilibrium position, piston 15 is capable only of threadable movement within barrel 11. When barrel 11 is moved away from the equilibrium position, however, piston 15 is freely movable within barrel 11. As will be described below, pulling or pushing on piston 15 tends to move barrel 11 away from its equilibrium position. Accordingly, if it is desired to quickly move piston 15 within barrel 11, piston 15 may simply be pushed or pulled in the desired direction and it will move freely in that direction. Once released, piston 15 will again be locked in place within barrel 15, capable only of threadable movement.

Figure 5:
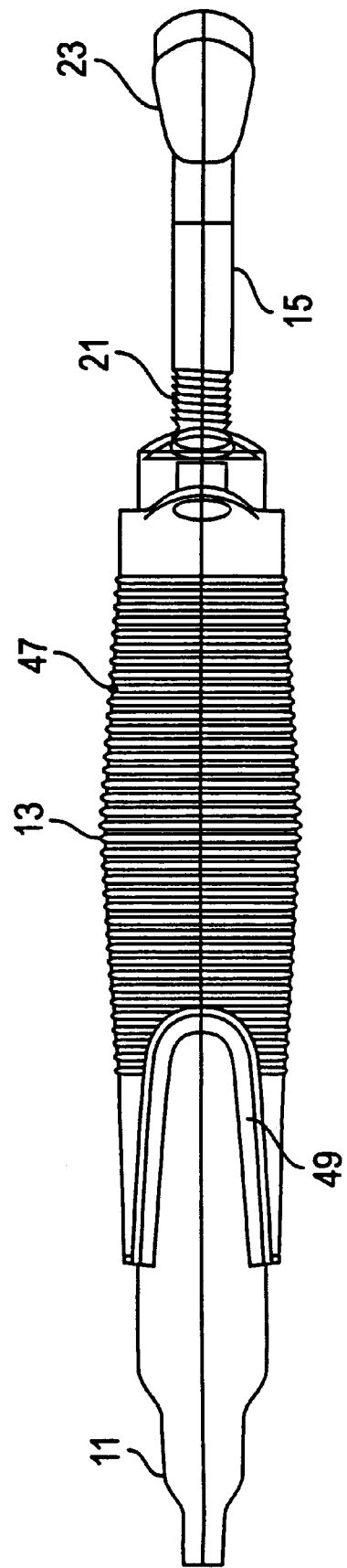
FIG. 5 is a top view of the inflation device of FIG. 2.

Barrel 11 is preferably cylindrical in shape, the term "cylindrical" including configurations in which barrel 11 (or any other element) is substantially cylindrical in shape. A distal end of barrel 11 is constructed to connect to and be placed in fluid communication with an inflatable member, for example a balloon catheter (not shown). Any known or suitable connection may be utilized for this purpose. The proximal end of barrel 11 may be open to accommodate piston 15. Collar 13 is also preferably cylindrical in shape, and may include an arcuate opening 49 that reveals the exterior surface of barrel 11. Opening 49, best shown in FIGS. 1 and 5, may then allow the operator to see graduated markings on the exterior surface of barrel 11.

Piston 15 is partially disposed within barrel 11, and preferably includes a piston head 17, a shaft 21, and handle 23. Piston head 17 is designed to retain a fluid within the distal portion of barrel 11, and may include any configuration which forms a seal against the interior surface of barrel 11. In the exemplary embodiment, piston head 17 includes a broad, conical distal end face and an o-ring 19, which is preferably disposed in an outer circumferential groove of piston head 17. Preferably o-ring 19 is compressible in order to maintain a resilient seal against the interior surface of barrel 11.

Figure 2:
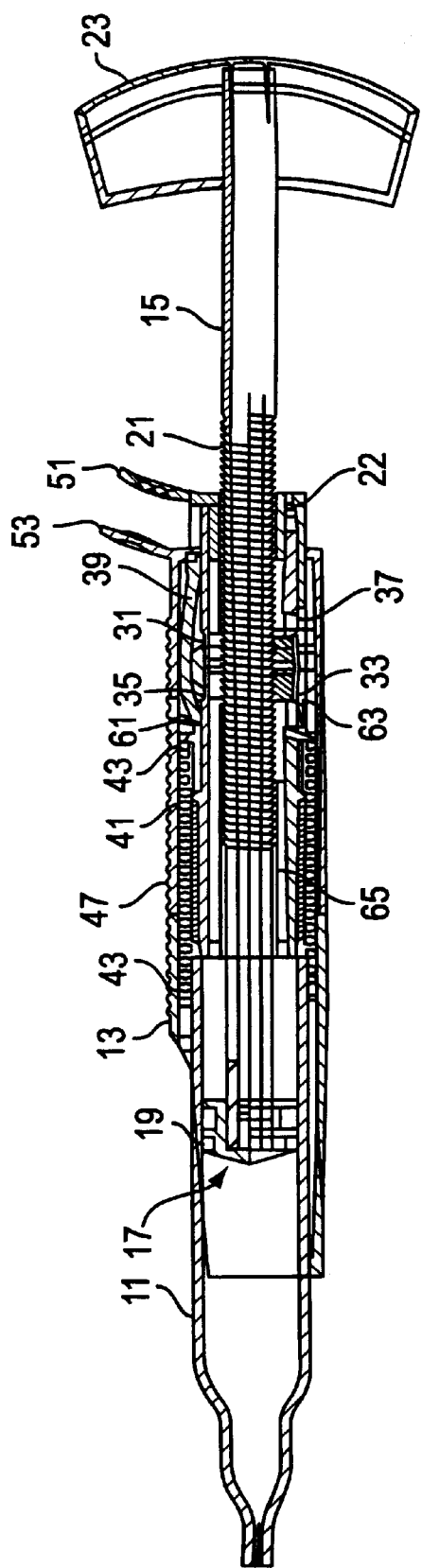
FIG. 2 is a side cross-sectional assembly view of an exemplary embodiment of an inflation device according to the present invention.
Figure 3:
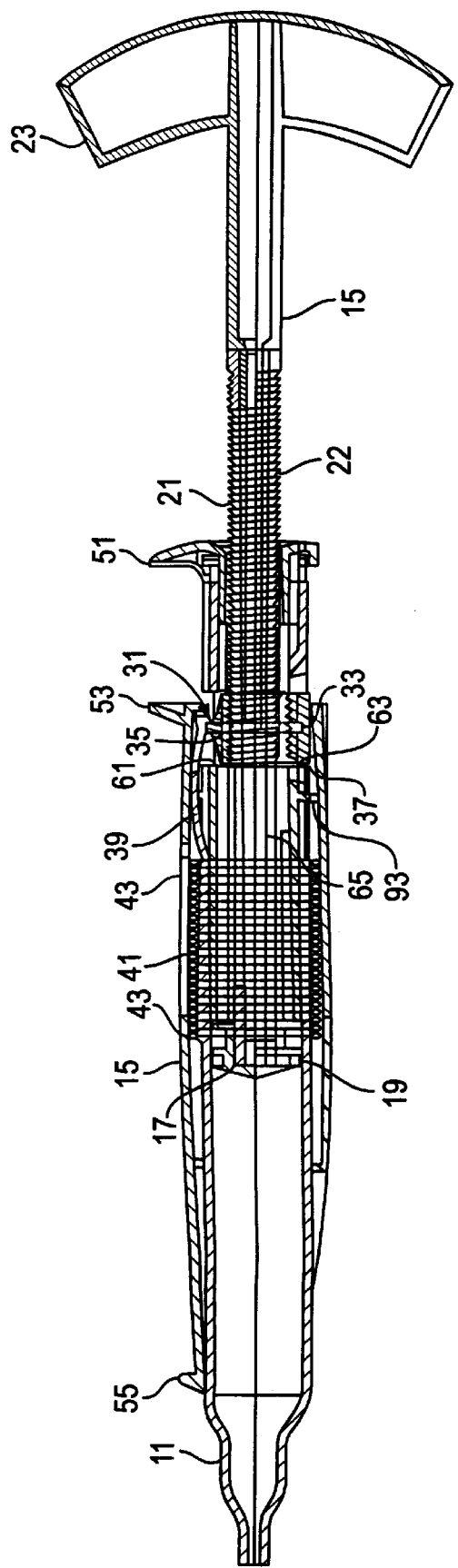
FIG. 3 is a side cross-sectional assembly view of a second exemplary embodiment of an inflation device according to the present invention.
Figure 4:
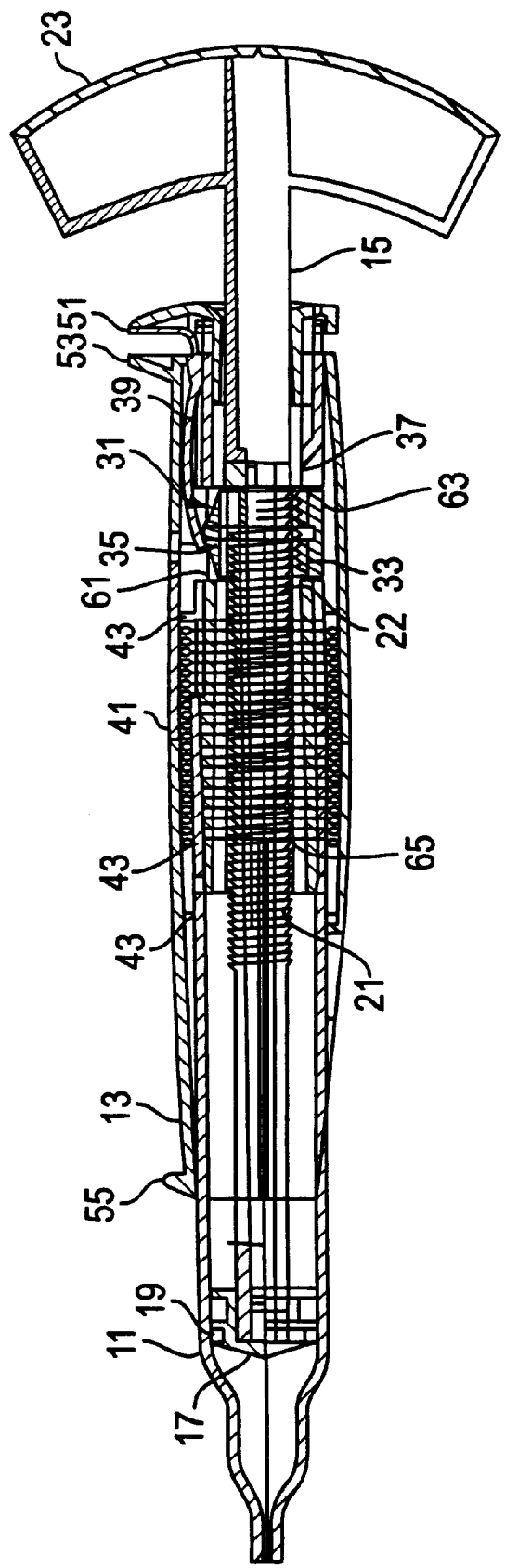
FIG. 4 is another side cross-sectional assembly view of the inflation device of FIG. 3.

In the illustrated embodiments of FIGS. 2 to 4, shaft 21 is supported within barrel 11 by an interior support structure 65 located in the proximal portion of barrel 11. In addition to stabilizing piston 15, support structure 65 may act as an abutment for piston head 17, preventing proximal movement of piston 15 beyond a desired point. Shaft 21 includes a threaded portion 22 that engages a threaded surface 33 of a nut 31, described in detail below. Because the inflation fluid used to inflate the inflatable member will often apply a force to piston 15 in the proximal direction, it is advantageous for the engagement between threaded portion 22 and nut 31 to particularly resist proximal movement of piston 15. To this end, threaded portion 22 preferably includes an asymmetrical thread in which the distal face of each thread is disposed at a higher angle with respect to the piston axis than the proximal face of the thread. This thread configuration is illustrated in each of FIGS. 2 to 4.

Handle 23 may be provided on the proximal end of shaft 21, if desired. Handle 23 may include any suitable formation, including a knob, a ring, or other graspable member capable of being manipulated by the operator. Preferably, however, handle 23 is a curved, elongated member disposed transverse to shaft 21, as illustrated in FIGS. 1 to 4.

Axial movement of piston 15 may be regulated by nut 31, which may also be provided within barrel 11. Nut 31 is preferably movable along an axis which is substantially transverse to barrel 11 and shaft 21. In order to prevent axial movement of nut 31, nut 31 is preferably maintained within a recess 63 of barrel 11, although nut 31 may be maintained in axial position in any suitable manner. It should be understood that "recess" includes any formation that minimizes or prevents axial movement of nut 31. Thus recess 63 may include, for example, one or more holes in barrel 11, positive structure disposed on the interior surface of barrel 11, or one or more indentations on the interior surface of barrel 11. In the illustrated embodiments, recess 63 is formed within support structure 65 and includes, for example, an opening shaped to support a nut spring 37.

Nut 31 includes, for example, an interior threaded surface 33 that selectively engages threaded portion 22. In general, "nut" should be read to include any element which includes such a threaded surface. Preferably, nut 31 also includes an exterior camming surface 35, which is preferably located substantially opposite interior threaded surface 33 with respect to piston 15. Nut 31 may extend through an opening 61 in barrel 11 so that exterior camming surface 35 may contact a collar camming surface 39. Collar camming surface 39 is therefore preferably aligned with opening 61, so that the protruding exterior camming surface 35 contacts collar camming surface 39. Preferably exterior camming surface 35 is provided as a smooth, convex surface that allows exterior camming surface 35 to slide smoothly along collar camming surface 39. Any suitable shape of exterior camming surface may be utilized, however. In order to maintain contact between camming surfaces 35 and 39, a nut spring 37 is provided to bias nut 31 towards collar camming surface 39, "nut spring" including any spring, elastic member, or other element capable of biasing nut 31 towards collar camming surface 39.

Collar camming surface 39 is preferably bi-directional, meaning that nut 31 is biased downwardly by collar camming surface 39 (as viewed in FIGS. 2 to 4) when nut 31 is moved either proximally or distally along collar camming surface 39. In particular, collar camming surface 39 is preferably a shallow, concave surface as shown in FIGS. 2 to 4. In addition, because the forces involved in pressurizing (inflating) the balloon and evacuating the balloon are different, collar camming surface 39 is preferably less inclined towards its proximal end than towards its distal end. This offers the operator greater mechanical advantage when evacuating the balloon. Alternatively, a shallow V-shaped or other suitably-shaped surface may be utilized. A bi-directional collar camming surface 39 need not be provided if free movement in only a single direction is desired. In that situation, a "uni-directional" camming surface may be provided.

In an unbiased, equilibrium position, which may be defined as its "home position," barrel 11 is disposed axially within collar 13 so that exterior camming surface 35 may be at or near a center point of the valley of collar camming surface 39. This position is illustrated in FIG. 2. Barrel 11 may be urged towards the equilibrium position by collar spring 41, which engages both barrel 11 and collar 13. In the illustrated embodiments, collar spring 41 is bordered by a plurality of abutments 43, which are disposed on the exterior surface of barrel 11 and the interior surface of collar 13. Abutments 43 may be radially spaced so that they do not interfere with one another as barrel 11 moves axially within collar 13. When barrel 11 is in its equilibrium position, nut 31 is in a "locking position" in which interior threaded surface 33 engages threaded portion 22 of shaft 21. When nut 31 is in the locking position, piston 15 is only capable of threadable movement within barrel 11. That is, piston 15 may be rotated, and rotation will produce fine axial movement.

FIG. 3 illustrates an inflation device with barrel 11 away from its equilibrium position, which in this Figure has been achieved by drawing piston 15 proximally. Proximal movement of piston 15 with respect to the collar 13 initially will move barrel 11 and piston 15 proximally within collar 13 (because barrel 11 and piston 15 are initially locked by nut 31). This proximal movement of barrel 11 and piston 15 causes nut 31 to travel along collar camming surface 39, biasing nut 31—and in particular interior threaded surface 33—downwardly (with respect to FIG. 3). Eventually, interior threaded surface 33 will no longer engage threaded portion 22, and piston 15 will become freely movable within barrel 11. It should be understood that "freely movable" merely designates a state in which piston 15 may move axially without being rotated, and includes movement in which piston 15 maintains some slight contact with interior threaded surface 33.

When the desired position of piston 15 is reached, the operator can simply release piston 15 while holding collar 13, or simply release the entire inflation device, if desired. Collar spring 41 will then urge barrel 11 to its equilibrium position, which in turn will allow nut 31 to return to the locking position (as illustrated in FIG. 2). Piston 15 then will be axially locked within barrel 11, capable only of threadable movement. In this manner, when it is desired to quickly deflate an inflatable member, the operator may pull piston 15 proximally to draw piston 15 to a desired position within barrel 11. Once a desired pressure is reached, the operator can release piston 15 or release the device as a whole. Barrel 11 will be urged to its equilibrium position by collar spring 41, and nut 31 will enter the locking position, thereby limiting axial movement of piston 15 to fine adjustment by the operator.

FIG. 4 illustrates the same principle in reverse, for example when it is desired to quickly move piston 15 distally to inflate a balloon catheter. Moving piston 15 distally into barrel 11 (i.e., to the left in FIG. 4) causes barrel 11 to move distally within collar 13. This movement in turn causes nut 31 to travel along collar camming surface 39, biasing nut 31 downwardly. Eventually, piston 15 becomes freely movable within barrel 11, and continues to move distally as long as it is pushed. When piston 15 is released, barrel 11 returns to the equilibrium position and nut 31 returns to the locking position, locking piston 15 in place.

An inflation device according to the present invention is thus extremely simple and convenient to use, because operation of the device is effectively transparent to the operator. Piston 15 may be moved proximally or distally very rapidly simply by applying force in the desired direction of movement. Once the desired position is reached, piston 15 may be locked in place by releasing it. At the same time, fine adjustment of piston 15 is achieved simply by rotating piston 15. Because the operator is not forced to actuate a separate trigger, button or switch, the operator is free to better concentrate on the task at hand.

Tabs 51 and 53 provide an additional method of depressurizing a balloon or, if the balloon has been evacuated to a vacuum state, pressurizing the balloon (i.e. eliminating the vacuum). In operation, an inflatable member such as a balloon may be maintained at a high pressure for some time. Alternatively, a balloon may be deflated to a vacuum state at times. These states may be negated by simply squeezing tabs 51 and 53 together to bias barrel 11 within collar 13. This will move nut 31 away form its locking position, allowing piston 15 to freely move within barrel 11 to depressurize or pressurize the balloon (depending on its initial state). Tabs 51 and 53 may be squeezed together with only one hand, allowing depressurization or pressurization even when an operator's other hand is occupied.

An inflation device according to the present invention may be constructed using any suitable materials and construction processes. Preferably, barrel 11 is formed from glass or a clear plastic such as polycarbonate. Collar 13 is preferably formed of ABS ( ), while piston may be formed of polycarbonate.

Figure 6:
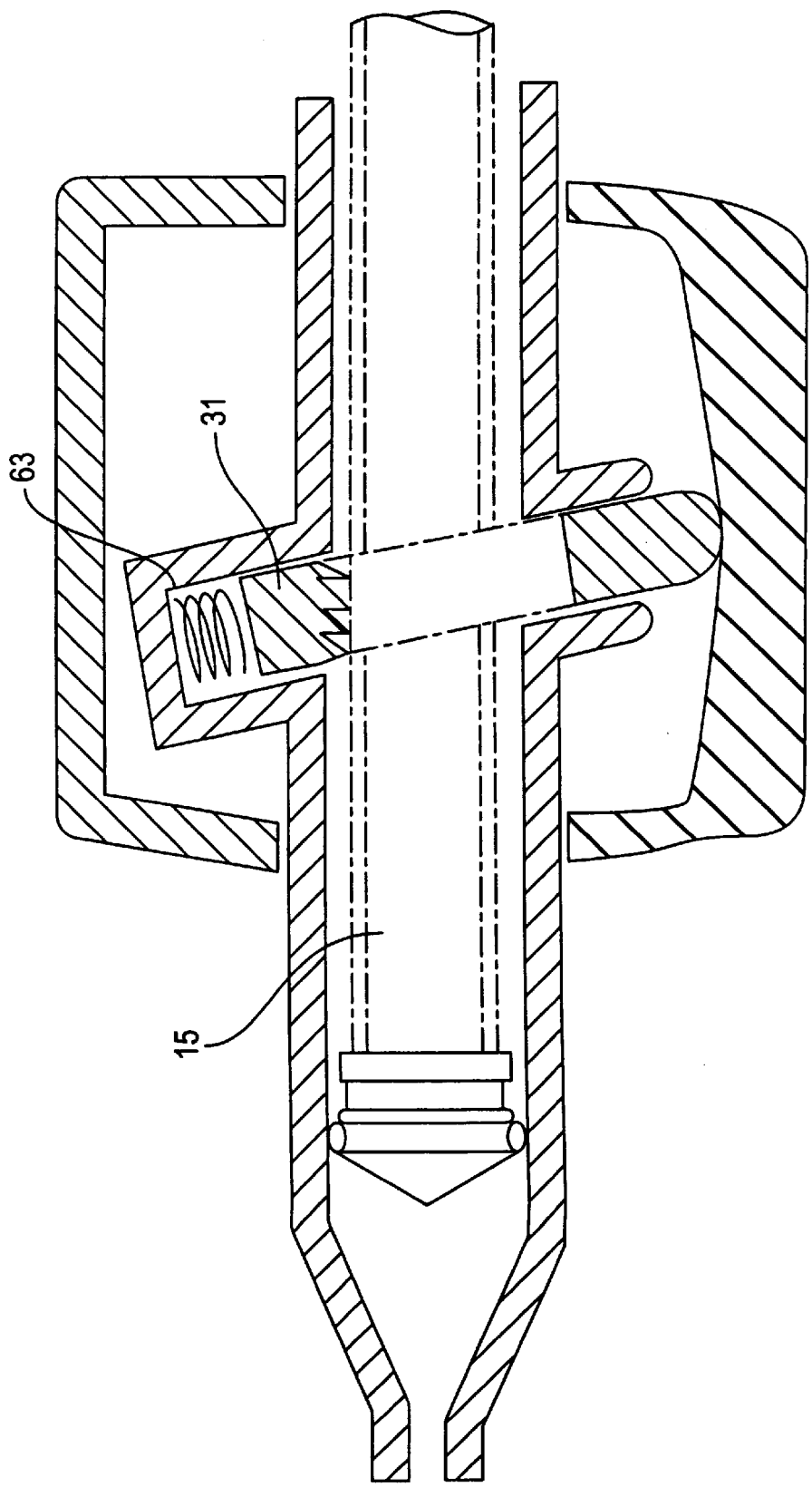
FIG. 6 is a schematic cross-sectional view of another exemplary embodiment of an inflation device according to the present invention.

FIGS. 6–13 illustrate additional embodiments of an inflation device according to the present invention. In FIG. 6, for example, recess 63 and nut 31 are disposed at a slight "backward angle" with respect to piston 15. In this orientation, back pressure from piston 15 will drive nut 31 against angled recess 63, which will deflect nut 31 downwardly (as viewed in FIG. 6). This downward force may enhance, for example, the engagement of interior threaded surface 33 and threaded portion 22. Alternatively, recess 63 and nut 31 could be maintained at a slightly "forward angle," in which back pressure from the piston tends to decrease the engagement of interior threaded surface 33 and threaded portion 22. A forward angle arrangement is particularly advantageous, for example, in high-pressure applications in which friction between the threads makes disengagement difficult.

FIGS. 7–13 illustrate several additional exemplary engagement mechanisms for controlling the engagement of nut 31 and piston 15. In each of these arrangements, engagement mechanism is coupled to barrel 11, collar 13, and piston 15. As with the mechanism described above, axial movement of barrel 11 within collar 13 disengages the engagement mechanism to allow free movement of piston 15 within barrel 11. Likewise, when barrel 11 is in its equilibrium position, piston 15 is axially locked within barrel 11, capable only of threadable movement. As with the mechanism described above, barrel 11 may be biased to its equilibrium position.

Figure 7:
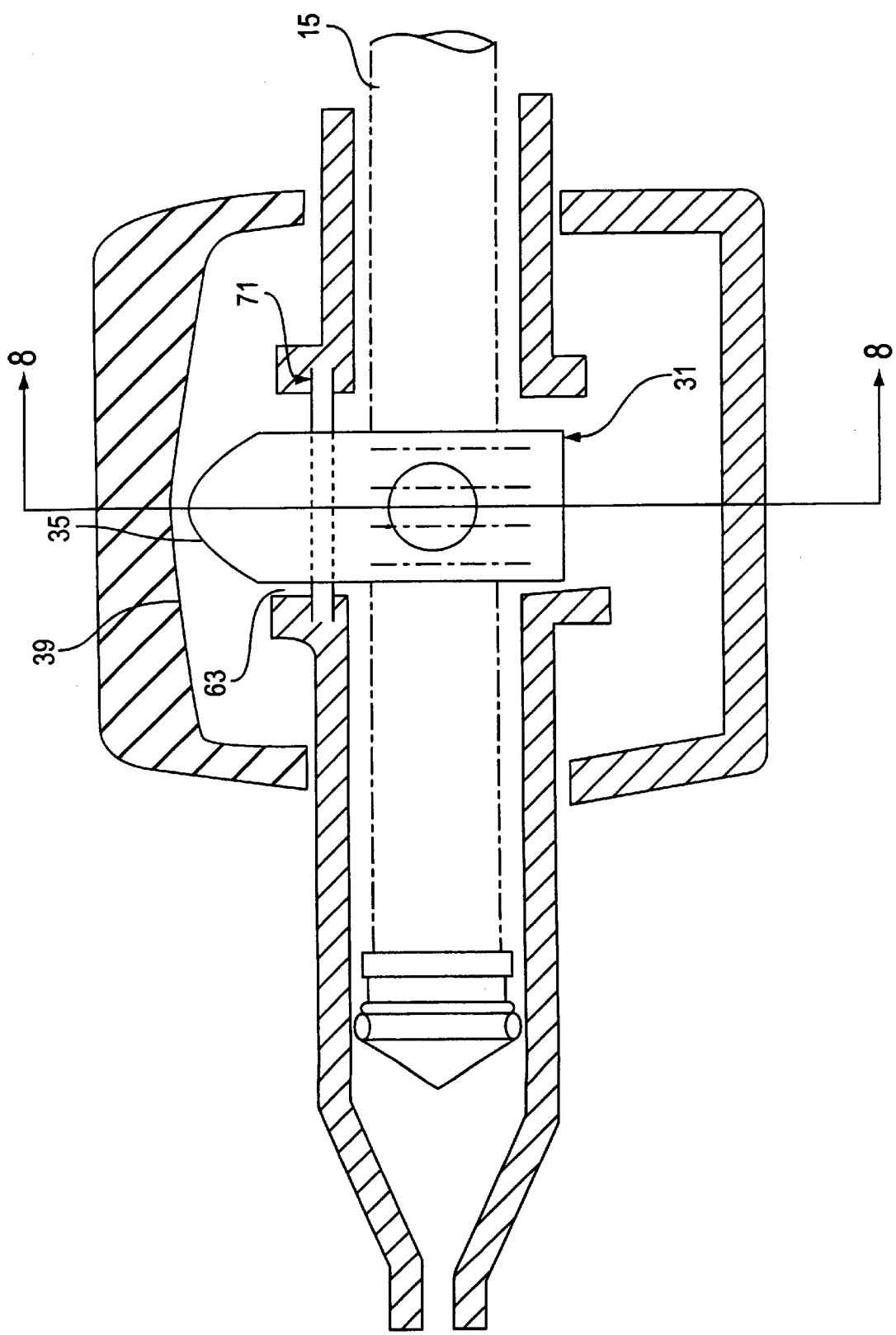
FIG. 7 is a schematic cross-sectional view of another exemplary engagement mechanism according to the present invention.
Figure 8:
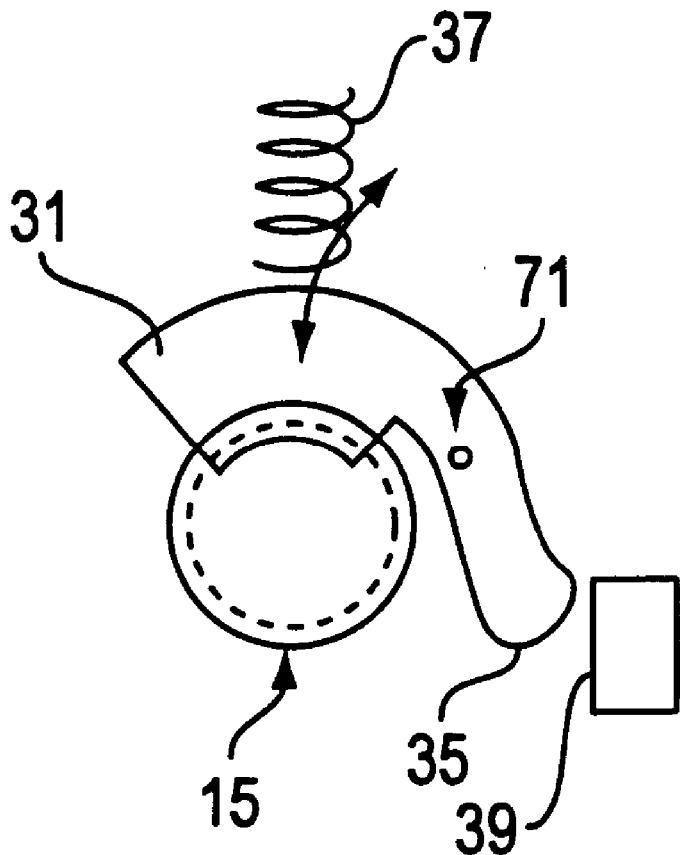
FIG. 8 is a view of the mechanism of FIG. 7, taken along line 8—8 of FIG. 7.

FIGS. 7 and 8 illustrate an engagement mechanism basically in the form of a lever. In particular, movement of exterior camming surface 35 along collar camming surface 39 causes nut 31 to rotate around a pin 71, disengaging nut 31 from piston 15.

Figure 9:
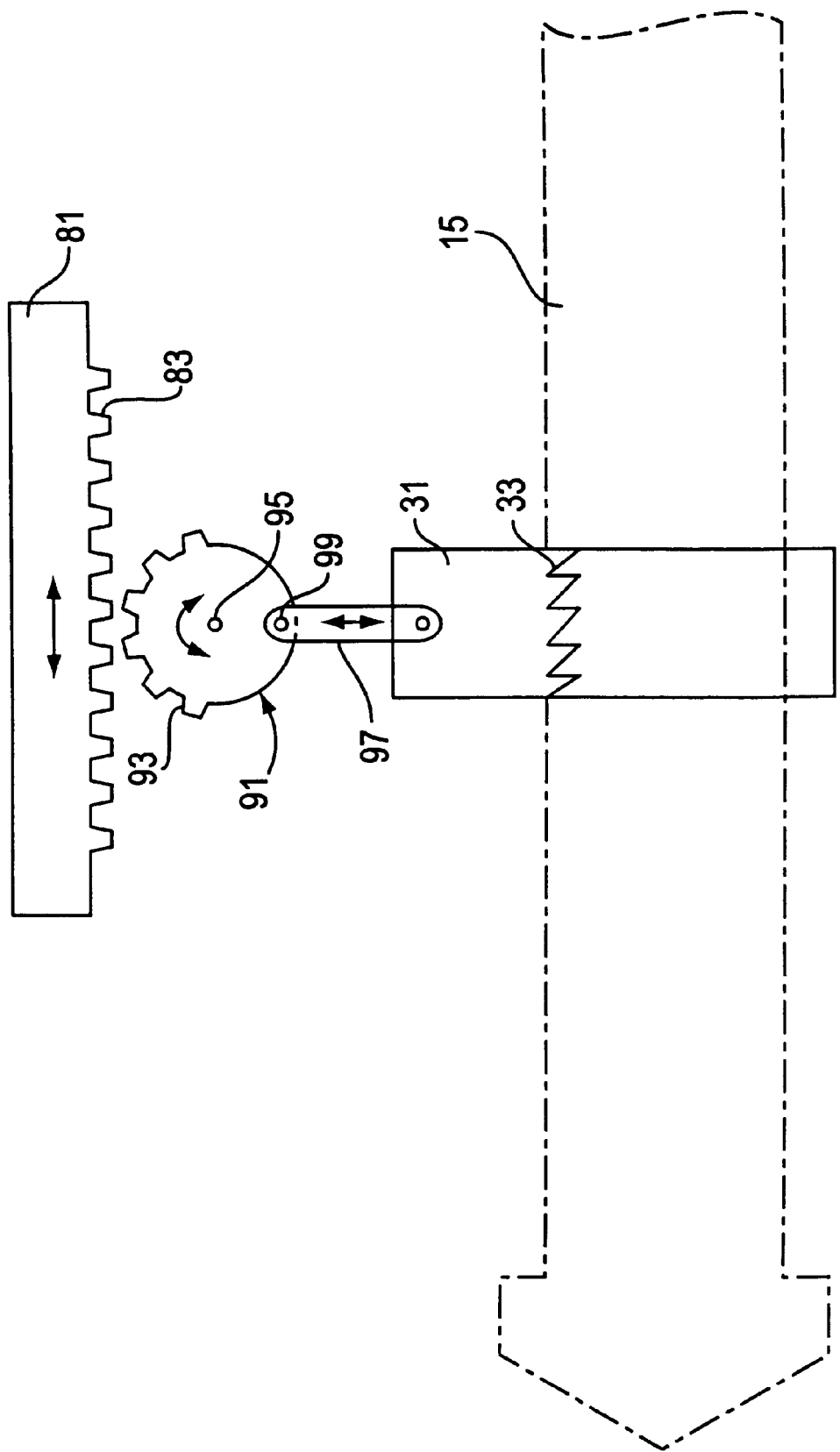
FIG. 9 is a schematic side view of a third exemplary engagement mechanism according to the present invention.
Figure 10:
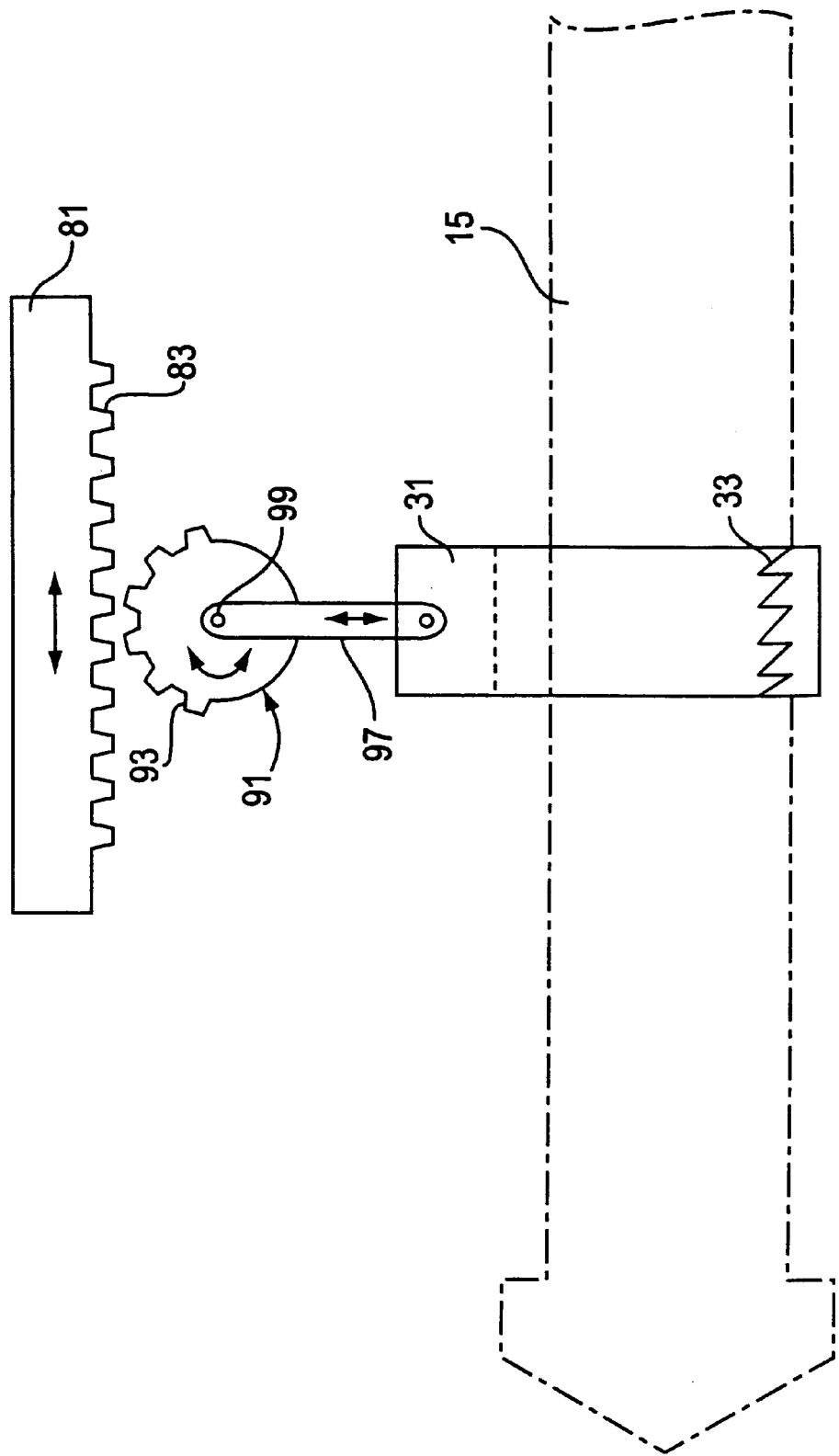
FIG. 10 is a schematic side view of a fourth exemplary engagement mechanism according to the present invention.

In other embodiments, there may be a direct linkage between nut 31 and collar 13. FIGS. 9 and 10, for example, illustrate engagement mechanisms in the form of a gear or rack and pinion arrangement. In FIG. 9, for example, rack 81 may be connected to collar 13, while gear 91 may be rotatably connected to barrel 11 through pivot 95. Link arm 97 is also connected to gear 91, for example at pivot 99. Rack teeth 83 cooperate with gear teeth 93 so that as barrel 11 is moved within collar 13, gear 91 rotates, causing link arm 97 to draw interior threaded surface away from piston 15. FIG. 10 employs essentially the same arrangement, with the exception that link arm 97 is connected to gear 91 on the opposite side of pivot 95, and interior threaded surface 31 is on the opposite side of piston 15. In this configuration, movement of barrel 11 within collar 13 causes link arm 97 to push (rather than pull) interior threaded surface 31 away from piston 15.

Figure 11:
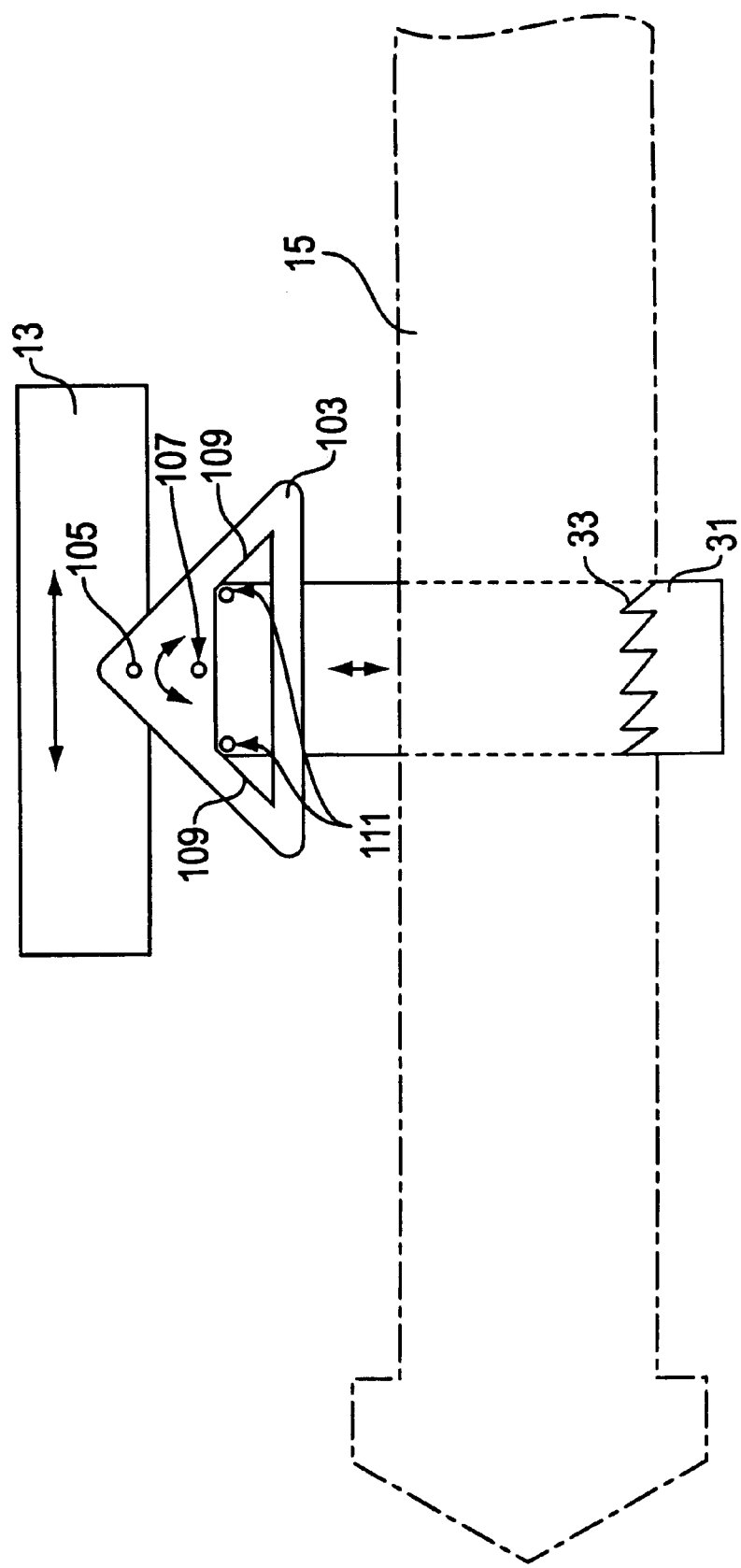
FIG. 11 is a schematic side view of a fifth exemplary engagement mechanism according to the present invention.
Figure 12:
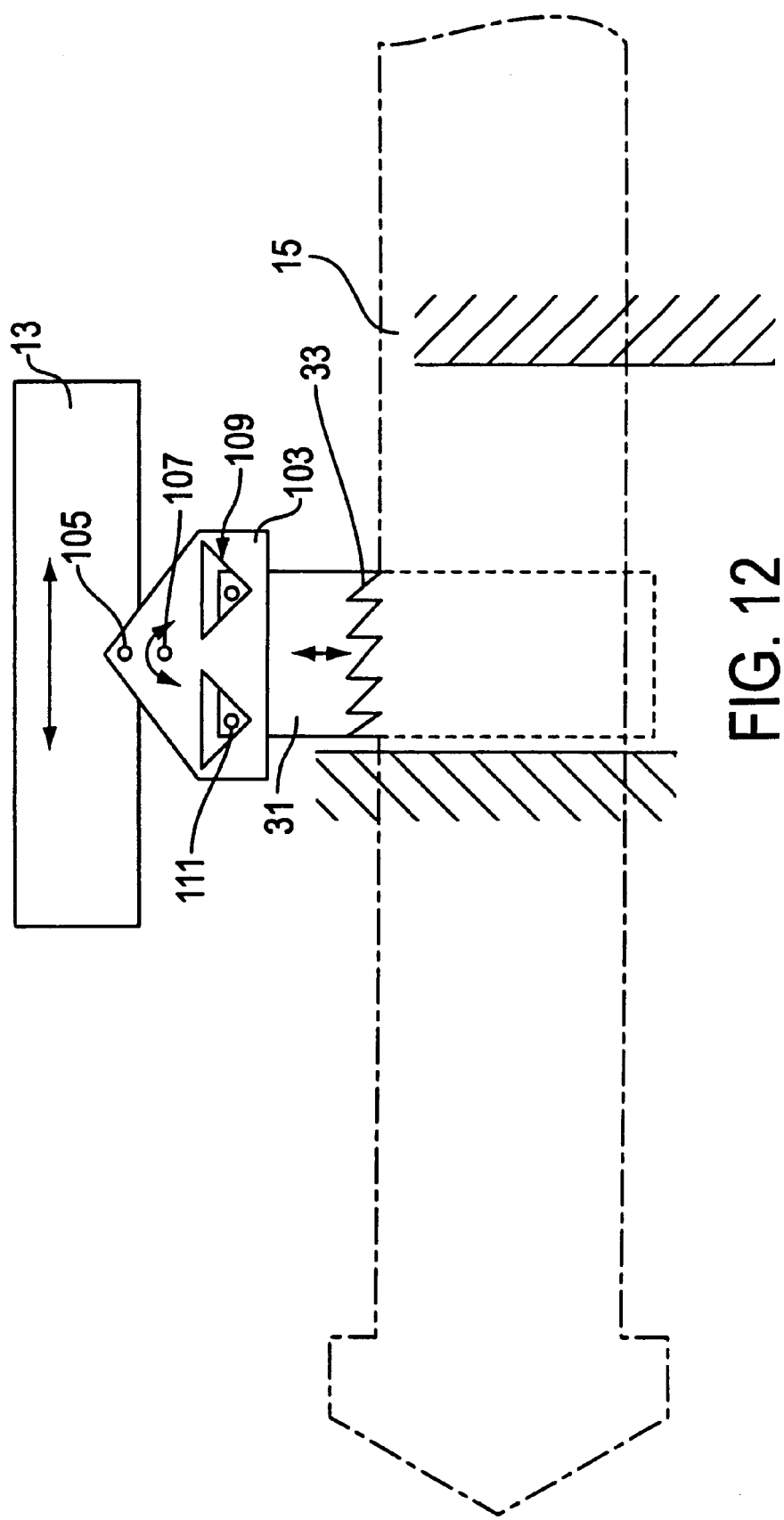
FIG. 12 is a schematic side view of a sixth exemplary embodiment of the engagement mechanism of FIG. 11.
Figure 13:
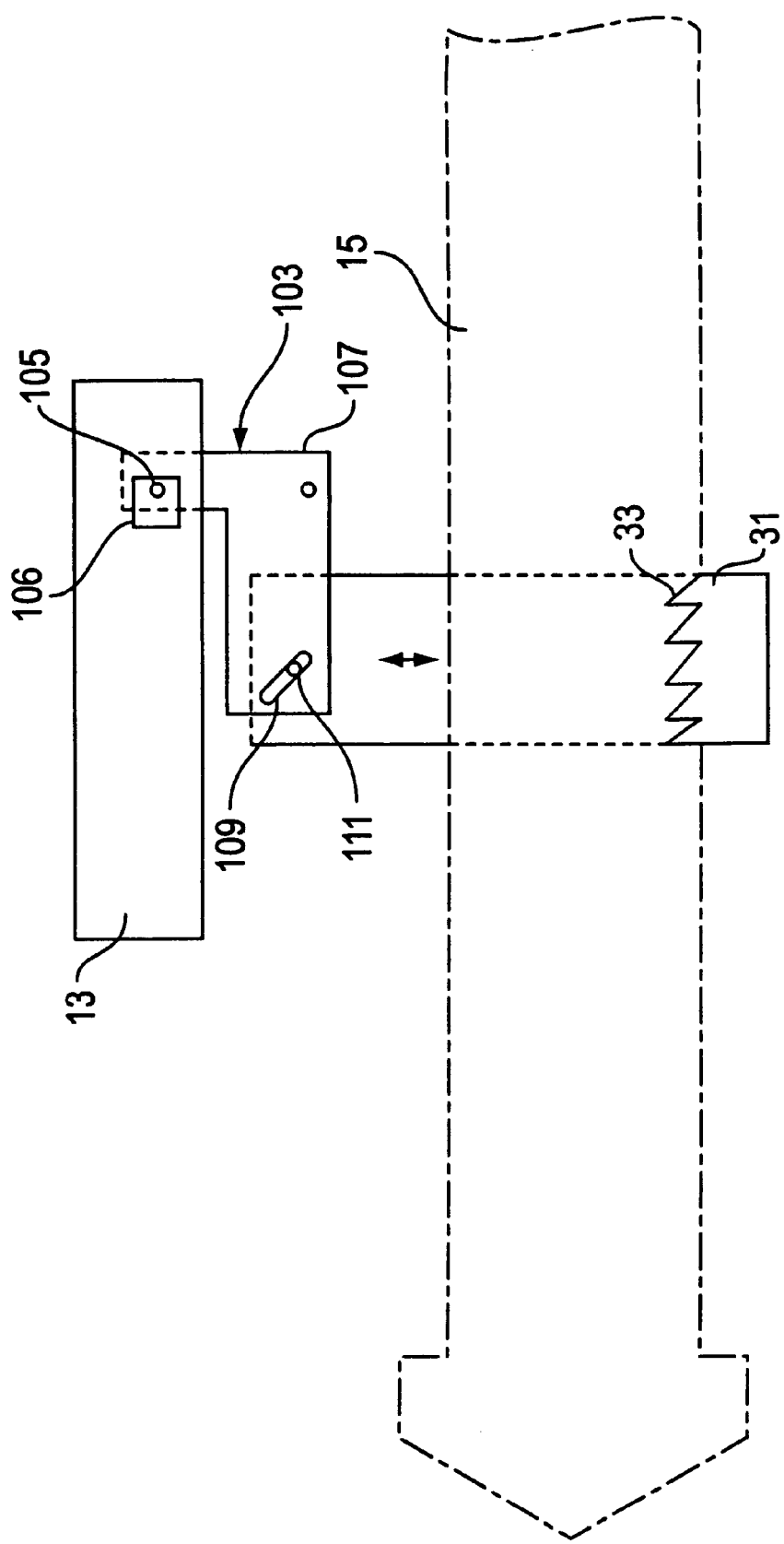
FIG. 13 is a schematic side view of a seventh exemplary engagement mechanism according to the present invention.

FIGS. 11 to 13 illustrate engagement mechanisms including linkage arrangements. In FIG. 11, for example, link member 103 is rotatably connected to collar 13 at pivot 105 and to barrel 11 at pivot 107. Pins 111, which are disposed on nut 31, project through a slot in link member 103 just below a slot contact surface 109. As barrel 11 is moved within collar 13, link member 103 rotates. Slot contact surface 109 contacts one of the pins 111, biasing nut 31 downwardly (as viewed in FIG. 11) so that interior threaded surface 33 disengages from piston 15. In FIG. 12, slot contact surfaces 109 are oriented in the opposite direction from those in FIG. 11, and interior threaded surface 33 is on the opposite side of piston 15. In this arrangement, movement of barrel 11 causes link member 103 to pull (rather than push) interior threaded surface 31 away from piston 15. In the embodiment of FIG. 13, link member 103 is formed in an L-shape, the arms rotating around pivot 107 to move interior threaded surface 33 into and out of engagement with piston 15 as barrel 11 moves within collar 13.

The device according to the present invention has been described with respect to several exemplary embodiments. It can be understood, however, that there are many other variations of the above-described embodiments which will be apparent to those skilled in the art, even where elements have not explicitly been designated as exemplary. For example, collar camming surface 39 could be a convex rather than concave surface, and interior threaded surface 33 could then be disposed on the same side of piston 15 as collar camming surface 39. In addition the inflation device may include additional features such as ridges 47 or a shoulder 55 to provide a secure grip for the operator. It is understood that these and other modifications are within the teaching of the present invention, which is to be limited only by the claims appended hereto.

What is claimed is:

1. An inflation device, comprising:
   a barrel having an axis;
   a collar surrounding at least a portion of the barrel, the collar and the barrel being axially movable with respect to one another, the barrel having an equilibrium position within the collar;
   a piston at least partially disposed within the barrel; and
   an engagement mechanism coupled to the barrel, the collar, and the piston;
   wherein when the barrel is in the equilibrium position, the engagement mechanism axially locks the piston within the barrel, and when the barrel is out of the equilibrium position the piston is freely moveable within the barrel.

2. The inflation device according to claim 1, wherein barrel and the collar are each cylindrical, and wherein the barrel is biased towards the equilibrium position.

3. The inflation device according to claim 2, wherein the engagement mechanism includes a nut connected to the barrel by a pin, the nut contacting a threaded portion of the piston to axially lock the piston when the barrel is in the equilibrium position, and wherein movement of the barrel within the collar causes the nut to rotate about the pin, disengaging the nut from the threaded portion of the piston.

4. The inflation device according to claim 2, wherein the engagement mechanism includes a nut coupled to the barrel via a gear, the nut contacting a threaded portion of the piston to axially lock the piston when the barrel is in the equilibrium position, and wherein movement of the barrel within the collar causes a rack of the collar to rotate the gear, disengaging the nut from the threaded portion of the piston.

5. The inflation device according to claim 2, wherein the engagement mechanism includes a nut coupled to the barrel via a link member, the link member being coupled to the collar, wherein the nut contacts a threaded portion of the piston to axially lock the piston when the barrel is in the equilibrium position, and wherein movement of the barrel within the collar causes the link member, disengaging the nut from the threaded portion of the piston.

6. An inflation device, comprising:
a barrel having a barrel axis, a proximal end, and a distal end;
a piston including a threaded portion, the piston being at least partially disposed within the barrel;
a collar surrounding at least a portion of the barrel, the collar and the barrel being axially movable with respect to one another, the barrel being biased towards an equilibrium position within the collar by a collar spring, and the collar including a collar camming surface; and
a nut coupled to the barrel, the nut including an interior threaded surface and an exterior camming surface, the nut being movable along an axis substantially transverse to the barrel axis and being biased towards the collar camming surface, the exterior camming surface contacting the collar camming surface;
wherein when the barrel is in the equilibrium position the nut is in a locking position which prevents free movement of the piston within the barrel, and when the barrel is moved from the equilibrium position the collar camming surface deflects the nut so that the piston is freely movable within the barrel.

7. The inflation device according to claim 6, wherein nut is at least partially disposed within a recess of the barrel.

8. The inflation device according to claim 7, wherein the nut is biased toward the collar camming surface by a nut spring.

9. The inflation device according to claim 8, wherein the interior threaded surface and the exterior camming surface are disposed on substantially opposite sides of the piston.

10. The inflation device according to claim 8, the piston further including a handle connected to a proximal end of the piston, wherein when the nut is in the locking position movement of the handle with respect to the collar moves the barrel from the equilibrium position.

11. The inflation device according to claim 10, wherein when the handle is pulled proximally with respect to the collar, the barrel moves proximally from the equilibrium position and the piston moves proximally with respect to the barrel.

12. The inflation device according to claim 8, wherein the collar camming surface is a bi-directional camming surface.

13. The inflation device according to claim 12, wherein the interior threaded surface and the exterior camming surface are disposed on substantially opposite sides of the piston.

14. The inflation device according to claim 12, further comprising handle connected to a proximal end of the piston, wherein when the nut is in the locking position movement of the handle with respect to the collar moves the barrel from the equilibrium position.

15. The inflation device according to claim 14, wherein when the handle is pulled proximally with respect to the collar, the barrel moves proximally from the equilibrium position and the piston moves proximally with respect to the barrel; and when the handle is pushed distally with respect to the collar, the barrel moves distally from the equilibrium position and the piston moves distally with respect to the barrel.

16. The inflation device according to claim 15, wherein the nut is disposed within the recess at an angle with respect to the barrel axis.

17. The inflation device according to claim 16, wherein the nut extends through an opening in the barrel to contact the collar camming surface.

18. An inflation device for a balloon catheter, comprising:
a cylindrical barrel having an axis, a proximal end, and a distal end, the distal end of the barrel being constructed to be placed in fluid communication with a balloon catheter, the barrel having a recess and an opening thereon, the recess and the opening being disposed substantially radially opposite one another;
a piston, including:
a piston head disposed within the barrel, the piston head maintaining a seal against an inner surface of the barrel;
a shaft having a threaded portion, the shaft being at least partially disposed within the barrel, a distal end of the shaft being connected to the piston head and a proximal end of the shaft extending outside the proximal end of the barrel; and
a handle connected to the proximal end of the shaft;
a cylindrical collar surrounding at least a portion of the barrel, the collar and the barrel being axially movable with respect to one another, the barrel being biased towards an equilibrium position within the collar by a collar spring;
a collar camming surface disposed on an inner surface of the collar, the collar camming surface being aligned with the hole in the barrel; and
a nut disposed at least partially within the recess of the barrel, the nut including an interior threaded surface and an exterior camming surface, the nut being movable along an axis substantially transverse to the barrel axis, the nut being biased towards the collar camming surface by a nut spring, and the exterior camming surface extending through the opening in the barrel and contacting the collar camming surface;
wherein when the barrel is in the equilibrium position the interior threaded surface of the nut is in a locking position in which the interior threaded surface of the nut engages the threaded portion of the shaft, preventing free movement of the piston within the barrel, and when the barrel is moved from the equilibrium position the collar camming surface deflects the nut so that the piston is freely movable within the barrel.

19. The inflation device according to claim 18, wherein the interior threaded surface and the exterior camming surface are disposed on substantially opposite sides of the piston.

20. The inflation device according to claim 18, wherein when the nut is in the locking position movement of the handle with respect to the collar moves the barrel from the equilibrium position.

21. The inflation device according to claim 20, wherein when the handle is pulled proximally with respect to the collar, the barrel moves proximally from the equilibrium position and the piston moves proximally with respect to the barrel.

22. The inflation device according to claim 18, wherein the collar camming surface is a bi-directional camming surface.

23. The inflation device according to claim 22, wherein the interior threaded surface and the exterior camming surface are disposed on substantially opposite sides of the piston.

24. The inflation device according to claim 22, wherein when the nut is in the locking position movement of the handle with respect to the collar moves the barrel from the equilibrium position.

25. The inflation device according to claim 24, wherein when the handle is pulled proximally with respect to the collar, the barrel moves proximally from the equilibrium position and the piston moves proximally with respect to the barrel; and when the handle is pushed distally with respect to the collar, the barrel moves distally from the equilibrium position and the piston moves distally with respect to the barrel.

26. The inflation device according to claim 25, wherein the recess of the barrel is disposed at an angle with respect to the barrel axis.

27. The inflation device according to claim 25, wherein the barrel includes a support structure which supports the piston, and wherein the recess of the barrel is formed in the support structure.

* * * * *